(12) United States Patent
Moran et al.

(10) Patent No.: US 8,231,579 B2
(45) Date of Patent: Jul. 31, 2012

(54) CANNULA SEALING APPARATUS

(75) Inventors: Stuart Moran, Yorkshire (GB); Michael White, Yorkshire (GB); David Maine, Yorkshire (GB)

(73) Assignee: Surgical Innovations Limited, Yorkshire (GB)

( * ) Notice: Subject to any disclaimer, the term of this patent is extended or adjusted under 35 U.S.C. 154(b) by 560 days.

(21) Appl. No.: 12/438,697

(22) PCT Filed: Aug. 20, 2007

(86) PCT No.: PCT/GB2007/050498
§ 371 (c)(1),
(2), (4) Date: Aug. 28, 2009

(87) PCT Pub. No.: WO2008/023200
PCT Pub. Date: Feb. 28, 2008

(65) Prior Publication Data
US 2010/0022959 A1 Jan. 28, 2010

(30) Foreign Application Priority Data

Aug. 25, 2006 (GB) .................................. 0616816.5
Mar. 19, 2007 (GB) .................................. 0705216.0

(51) Int. Cl.
*A61M 5/178* (2006.01)
(52) U.S. Cl. ................................................ 604/167.01
(58) Field of Classification Search ........... 604/167.01–167.03, 164.01–166.01, 604/167.04–278; 606/205–207
See application file for complete search history.

(56) References Cited

U.S. PATENT DOCUMENTS

| 5,201,714 | A | 4/1993 | Gentelia et al. |
| 5,512,053 | A | 4/1996 | Pearson et al. |
| 5,569,206 | A | 10/1996 | Gorman, Jr. et al. |
| 5,607,397 | A | 3/1997 | Stephens et al. |
| 5,843,040 | A * | 12/1998 | Exline ...................... 604/164.11 |
| 2006/0147283 | A1 * | 7/2006 | Phillips .......................... 408/35 |

FOREIGN PATENT DOCUMENTS

| EP | 0673626 A1 | 9/1995 |
| WO | 9304717 A1 | 3/1993 |
| WO | 9417844 A1 | 8/1994 |
| WO | 9532011 A1 | 11/1995 |
| WO | 9604039 A1 | 2/1996 |

* cited by examiner

*Primary Examiner* — Manuel Mendez
(74) *Attorney, Agent, or Firm* — Shumaker, Loop & Kendrick, LLP

(57) ABSTRACT

A cannula sealing apparatus includes a housing having a central axially facing aperture. A surgical instrument of 10.5 mm may seal with that aperture. Alternatively, a sealing member having an aperture that will seal with a 12 mm surgical instrument can be swung up to be aligned with the aperture. If a 10.5 mm instrument is required then a seal member can be swung up to have its seal aperture located over the central aperture. Each seal member is pivotal about a common axis.

20 Claims, 6 Drawing Sheets

CANNULA SEALING APPARATUS

BACKGROUND OF THE INVENTION

The present invention relates to cannula sealing apparatus and methods of using cannula sealing apparatus. The present invention is particularly suited to such apparatus where surgical instruments of different sizes are required to be sealed with the same cannula sealing apparatus.

U.S. Pat. No. 5,512,053 describes a surgical cannula with a slidable reducer assembly to sealingly accommodate surgical instruments. The reducer assembly consists of multiple apertures having varying diameters such that the assembly can slide to selectively accommodate the exterior of surgical instruments having a variety of outer diameters.

U.S. Pat. No. 5,843,040 discloses a surgical sleeve that includes a housing having an opening through which surgical instruments are introduced into the surgical sleeve. A sleeve portion extends from the housing and has an inner diameter coaxial with the opening in the housing. A reducer assembly is removably secured to the housing and includes a rigid seal for rotation in a plane transverse to the sleeve portion. A resilient, laminar seal layer is generally coextensive with the seal disc and is disposed between the disc and the housing to sealingly engage a portion of the housing. A plurality of apertures are formed in the seal disc and seal layer and have varying diameters to define seals that are selectively movable, by rotation of the seal disc, over the opening in the housing to seal against exteriors of instruments disposed in the sleeve.

U.S. Pat. No. 5,201,714 provides a cannula for laparoscopic surgery wherein the cannula comprises a housing and an elongated tube with a passageway formed within the housing so that laparoscopic instruments may be passed through the housing and the elongated hollow tube into the abdominal cavity of a patient. A pair of rollers are mounted within the housing, the rollers being spring-urged together to close the passageway through the housing when an instrument is withdrawn. A slidable plate having apertures of different sizes are mounted in the housing with the apertures provided with slitted seals therein to close the passageway through the housing. The varying sized apertures in the slidable plate permit laparoscopic instruments of varying diameters to be used and to maintain an effective seal around the instrument.

WO 94 017 844 discloses a seal for use with a surgical instrument to provide a gas tight seal with the instrument having a diameter within a wide range of diameters. The seal comprises a seal body, an instrument seal, and a laterally compliant seal mounting. The seal body includes a bore through which the instrument is passed. The instrument seal extends radially outwards from an instrument port formed in the instrument seal through which the instrument is passed, and also extends axially from the instrument port in the direction opposite to that in which the instrument is passed through the instrument port. The laterally compliant seal mounting mounts the instrument seal to the seal body, forms a gas tight seal between the instrument seal and the seal body, and allows the instrument seal to move freely laterally in response to lateral movement of the instrument.

U.S. Pat. No. 5,607,397 and U.S. Pat. No. 5,569,206 disclose adaptors that can be attached around the cannula handle. The adaptors include a smaller seal that projects to one side of the handle and which can be pivoted over the handle about an axis perpendicular to the elongate axis of the cannula and to one side of that axis.

It is an object of the present invention to attempt to overcome at least one of the problems associated with the above publications or other problems.

SUMMARY OF THE INVENTION

The present invention is defined in the claims appended hereto and elsewhere in the specification.

According to one aspect of the present invention a cannula sealing apparatus includes a plurality of seal members each having a different sized aperture with which, in use, surgical instruments of different sizes may be inserted in a first direction to seal with a selected seal member, at least one seal member being pivotable from an operative position in which a surgical instrument may, in use, be inserted in the first direction to seal with that member and an inoperative position characterised in that the pivot axis of the pivotal movement of the sealing member is in a second direction, transverse to the first direction.

The second direction may be perpendicular to the first direction.

The opening in the housing may comprise a seal member.

The pivotally movable seal member may include a surface that is arranged, in use, to surround and seal with the surface of the housing that surrounds the opening and at least one surface may include a resilient member.

The apparatus may include a valve arranged, in use, to inhibit the flow of gas in at least one direction when no surgical instrument is being sealed by a seal member.

The or each seal member may be movable by a surgeon's instrument.

Where pivotal movement of the seal is restricted by a friction member the friction member may be located on the housing. The friction member may engage with the pivotal member or members. The friction member may be resilient.

Engagement of a friction member when the pivotal member moves between the positions may cause the friction member to deform and when the pivotal member moves from the inoperative position to the operative position during at least part of that movement the friction member may have no effect.

The pivotal member may include a channel spaced from a recess whereby, when moving the pivotal member from the inoperative to the operative position the relative movement causes the pivotal member to first be located in a channel then to frictionally engage the space between the channel and a recess and then to engage with the recess. The friction member may be located in the recess when the pivotable seal is in the useable position. The channel may comprise an end section that is ramped so as to initiate deformation of the friction member. The friction member may comprise at least one resilient nipple.

Where the resilient seal is circular and is supported by an adjacent non-resilient raised circular support of greater diameter than the resilient seal with the resilient seal being biased towards the circular support the resilient seal may include a circular hole for sealing against the instruments.

The resilient seal may include a circular opening that is supported by an adjacent non-resilient circular support of greater diameter than the resilient seal and the circular position may be raised. The resilient seal may be biased towards the circular support and the distance between the opening of two resilient seals and the openings of their supports may be the same. The part that the seal is mounted on may include at least one clip and the movable seal may include at least one corresponding opening that is expandable over the clip to retain the movable seal on the housing. Where a friction member is included at least one resilient seal may include the friction member.

The housing may include a resilient seal.

The or each pivotable member may include a resilient seal.

The opening in the housing may comprise a seal member.

The seal members may be provided on a first part of the apparatus that is detachable from a second part of the apparatus. A valve may be arranged to inhibit a flow of gas in at least one direction when no surgical instrument is being sealed by a seal member. At least one seal member may be arranged to be movable by the instrument of a surgeon.

The resilient seal or seals may include a circular hole for sealing against the instruments.

The or each pivotable member may include a resilient seal.

DESCRIPTION OF THE DRAWINGS

The present invention may be carried into practice in various ways but one embodiment will now be described with reference to the accompanying drawings, in which.

DETAILED DESCRIPTION OF THE INVENTION

Figures 1, 2, 3:
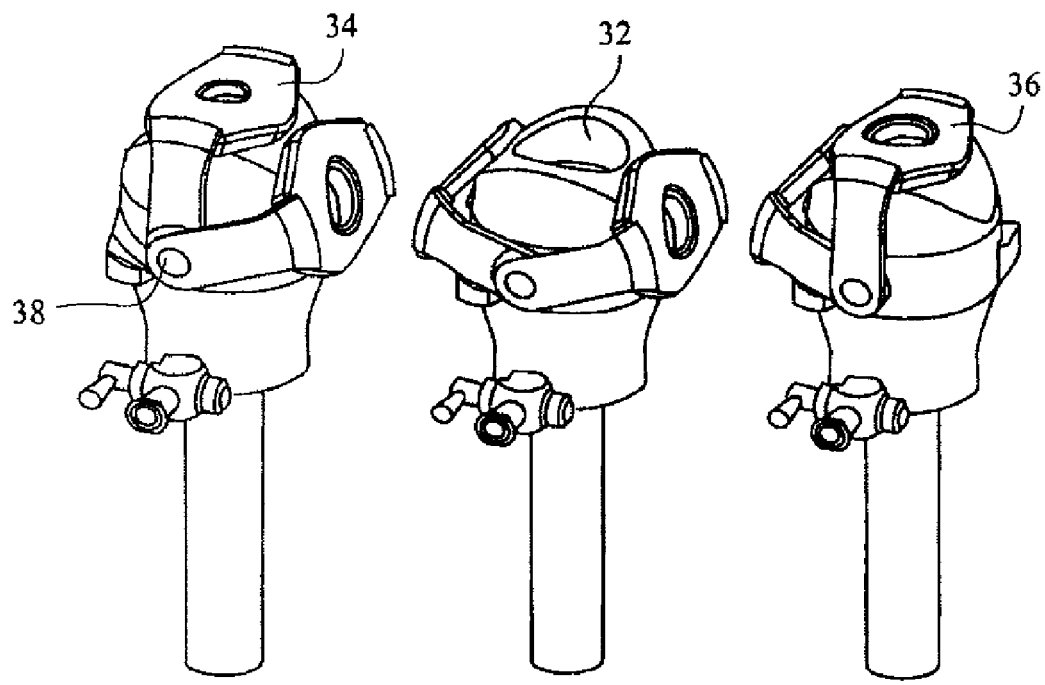
FIGS. 1, 2 and 3 are perspective views of a cannula sealing apparatus 10 arranged to receive instruments of different sizes.
Figure 4:
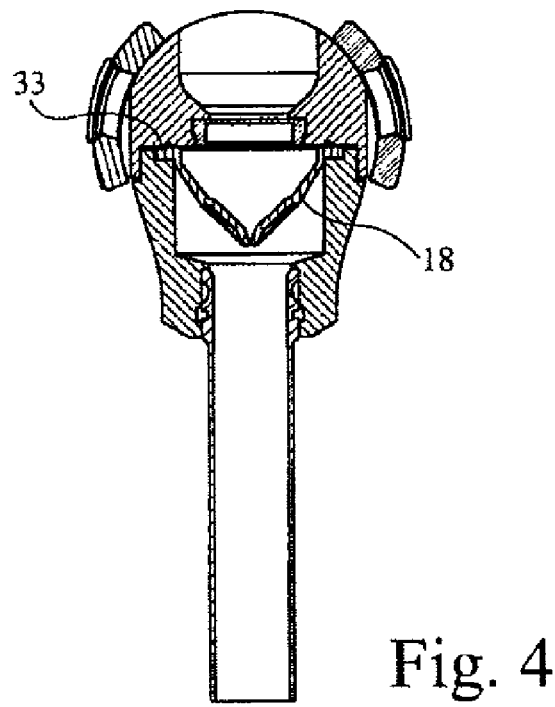
FIG. 4 is a sectional view through the apparatus.

A reusable cannula 14 has an upwardly facing opening 16 in which a valve 18 is located with an outwardly projecting lip 20 on the valve sitting on an upwardly facing annular rim 22. A gas input/output line 24 is connected to the cannula just below the valve 18 and an on/off valve 26 is provided on the line 24.

A single use seal housing 28 is detachably connected to the reusable cannula 14 with a bayonet connection comprising circumferentially spaced projections (not shown) 30 on the housing 28 cooperating with outwardly facing circumferentially spaced recesses 31 on the cannula such that the housing 28 can first be pushed down on the cannula with the projections moving along axially extending recesses and then with the housing 28 being rotated relative to the cannula. The projections then move along circumferentially extending recesses until end stops are reached. This locks the housing on the cannula. This also traps and seals the lip 20 on the rim 22 with an axially facing annular surface 33 of the housing compressing the resilient lip slightly.

The housing 28 includes a central axially facing aperture 32. Two arcuate seal members 34 and 36 are pivotally mounted on the housing by pivot members 38 at each side. End stops 35 limit pivotal movement in one direction. The pivot members extend perpendicularly to the axis of the cannula and radially to that axis and, from the outside towards the axis they extend first through an arm 42 of the seal member 36 and then through an arm 40 of the seal member 34 and then through the housing.

Figure 5:
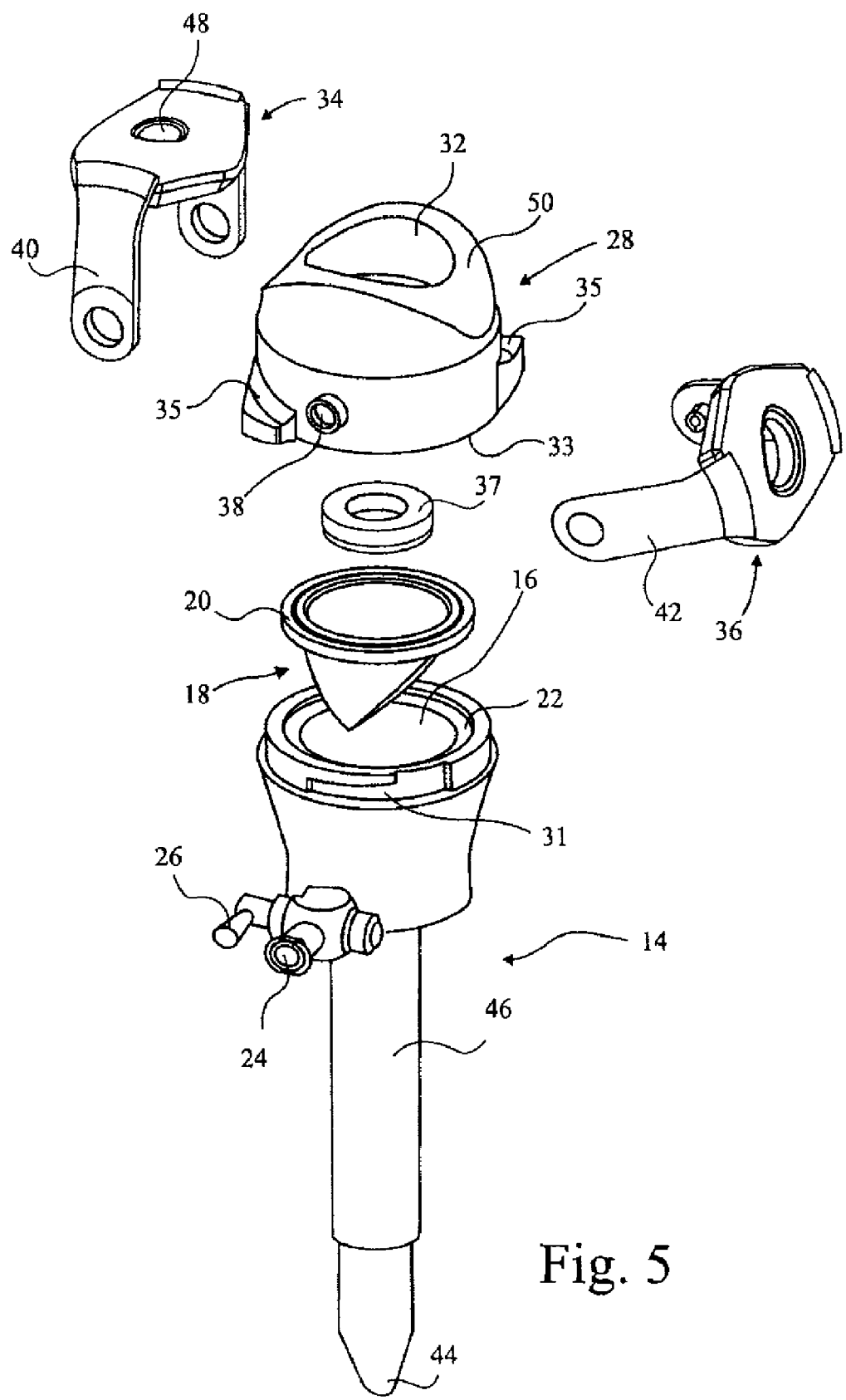
FIG. 5 is an exploded view of FIG. 1.

In use, the housing is connected to the cannula. A tip 44 of trocar instrument (only the bottom part of which is shown) in FIG. 5 is pushed first through the opening 32 in a first direction then through the valve 18 and then along and through an elongate tube 46 of the instrument to the position shown in FIG. 5. The instrument is then inserted through an opening in the abdominal wall with the trocar instrument expanding that opening and with the exterior of the tube 46 sealing with the abdominal wall opening. The periphery of the trocar seals with a sealing element 37 mounted in the opening 32 of the housing. Alternatively the trocar can be inserted through the opening 32 when the tube 46 already extends through the abdominal wall.

The on/off valve 26 is opened and gas is supplied through the inlet. This gas flows between the trocar on the tube 46 to inflate the abdominal cavity. Endoscopic operations with any endoscopic instrument including a camera instrument can then be carried out in a well known manner.

When the trocar is withdrawn back through the opening 32 the valve 18 effects a seal such that gas from the abdominal cavity is unable to escape.

The opening 32 also comprises a seal member 37 in addition to the pivoting seal members 34 and 36. Each seal member includes a membrane (not shown) that extends inwardly and that is resilient such that the trocar is able to seal with that opening. Whilst the description so far has been in relation to trocar instruments it will be appreciated that any instrument used in endoscopic surgery may be used with the cannula sealing apparatus.

The diameter of the opening 32 is such that instruments of nominal 12 mm diameter can seal with that opening as shown in FIG. 2. In some instances though instruments of different diameter may be required to seal with an opening in the region of the opening 32.

Figure 6:
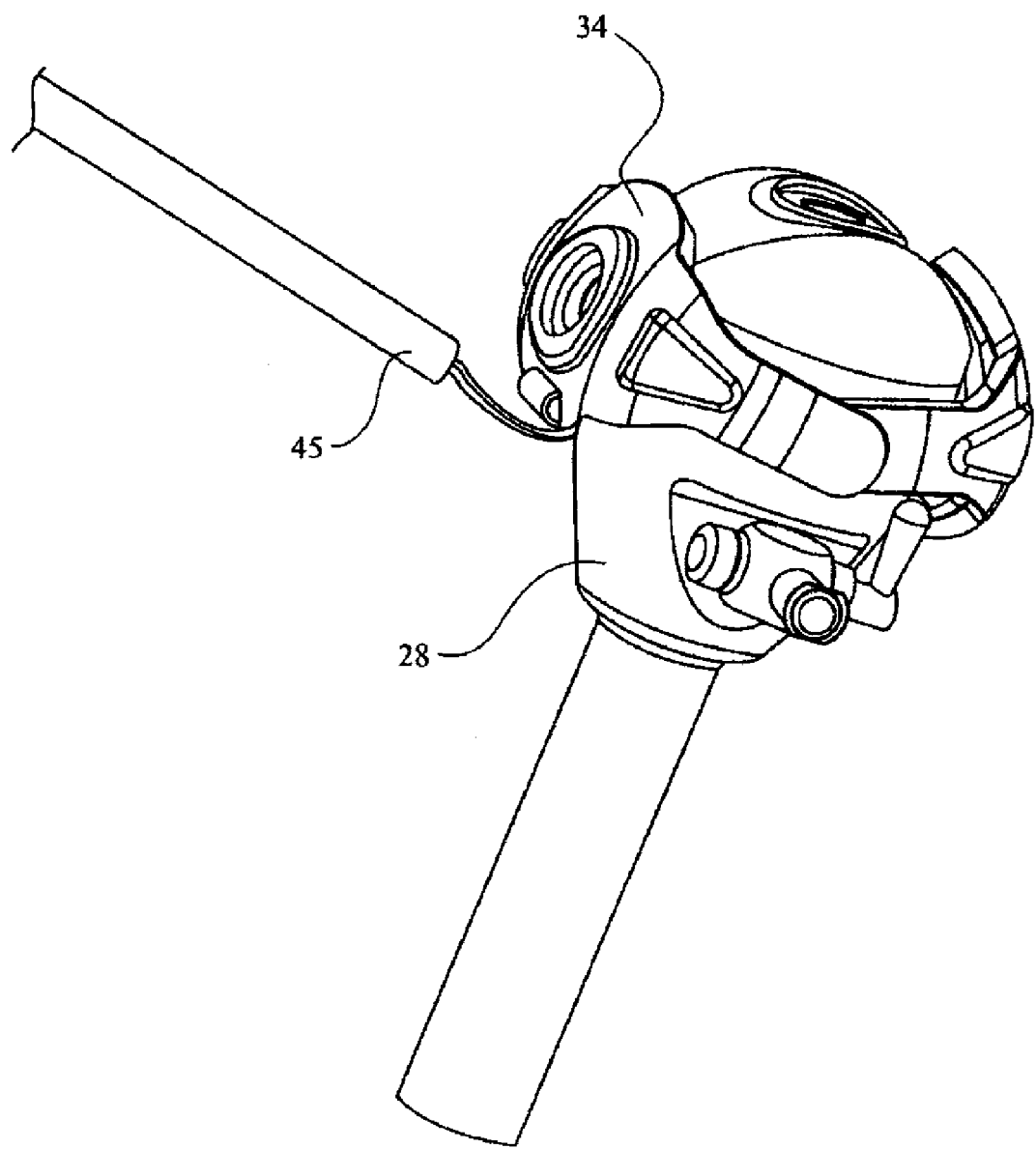
FIG. 6 is a perspective view of the cannula being operated by the instrument.
Figure 7A:
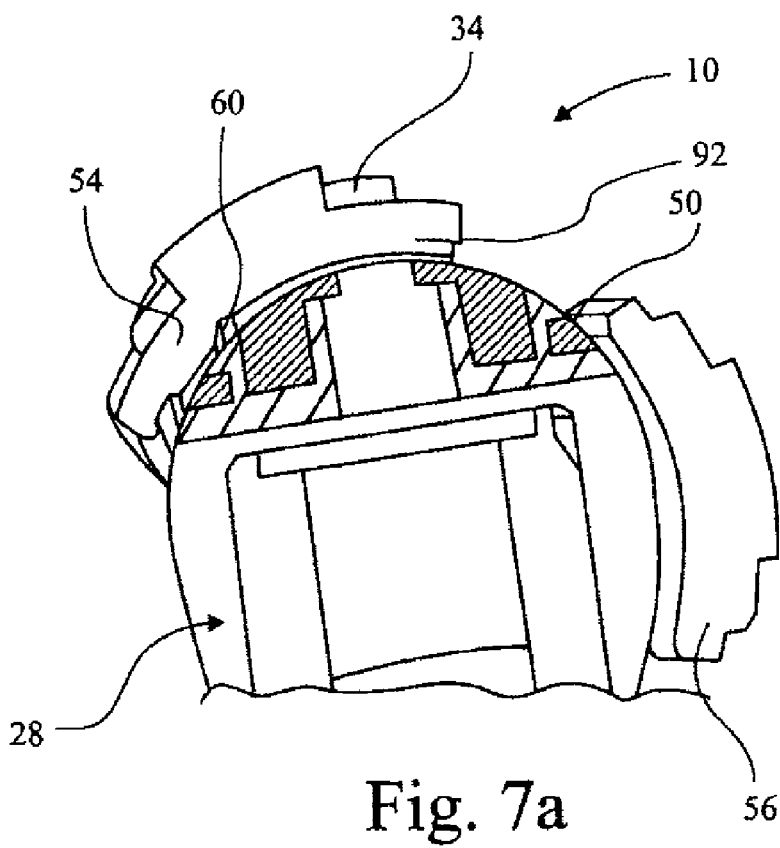
FIGS. 7a and 7b are cross-sectional views of a cannula sealing apparatus 10 according to a second embodiment showing the pivot members in different positions.
Figure 7B:
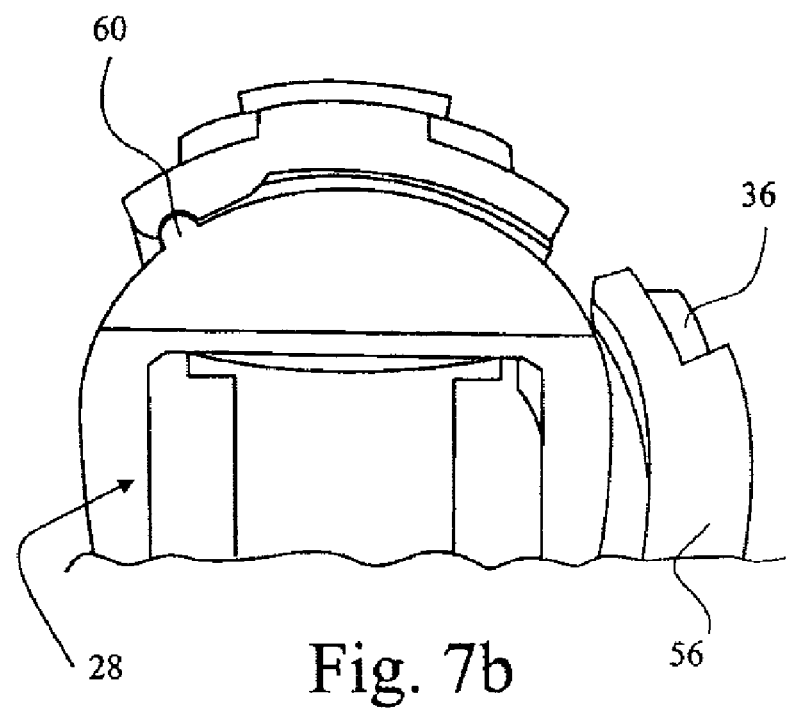

When a nominal 5 mm diameter instrument is to be used the seal member 34 is moved upwardly about the pivot members 38 until the centre of the nominal 5 mm diameter aperture 48 is coincident with the elongate axis of the tube 46 as shown in FIG. 1. A nominal 5 mm instrument can then be used with that instrument sealing with the seal member 34. Similarly a nominal 10 mm diameter instrument can seal with the seal member 36 by pivoting the member 34 back to the position shown in FIG. 2 and moving the seal member 36 up over the opening 32 as shown in FIG. 3. The movement of each seal member may be initiated either by hand or by the end of the surgeon's instrument. In the lattercase, as shown in FIG. 6, the tip 45 of the instrument abuts a side face of the respective seal member 34 and relative movement between the instrument and housing 28 affects the rotation of the seal member.

The selection of a tailored seal for each trocar diameter means the feel to the surgeon pushing the instrument in or withdrawing the instrument from a seal member is the same, regardless of the diameter of that member.

The facing surfaces of the housing 28 and the seal members 34 and 36 must seal when the openings of the members are concentric with the openings 32 of the housing.

To this end, whilst the arms 40 and 42 are at different axial extents relative to the axis of pivotal movement, the arcuate surfaces of the seal members that can face the opening 32, have the same part cylindrical or part spherical surface as a part cylindrical or part spherical surface of the housing in the region shown by the line 50. A soft sealing surface that may be slightly resilient is applied to the surfaces of the seal members that seal with the housing. This gives a constant feel to the switching of one opening member or another.

Whilst two pivoting seal members have been described there may be more or less than two seal members with, for instance, when there are three pivotable seal members each of which may be located over the fixed central aperture 32, two of those members may be located to a common side of that aperture. At that side, when the member furthest from the aperture 32 is required to be used, the one nearest to the aperture 32 may first be moved over and past that aperture 32 with movement of the previously furthest member then being moved over the central aperture.

Whilst apertures of nominal 5, 10 and 12 mm diameter have been described it will be appreciated that apertures of any diameter may be provided such as 5, 7, 10, 12 and 16 mm. The larger diameter openings are particularly suited to operations effected on obese patients. Furthermore the seals maybe colour coded, so that the surgeon may easily select the correct seal size by visual reference to the colour.

FIGS. 7 to 10 show a second embodiment of a cannula. The cannula is substantially in accordance with the first embodiment herein described wherein a single use housing 28 is detachably connected to a reusable cannula. However, rather than the arcuate seal members being pivotally mounted to the housing the seal members 34, 36 are mounted to rockers 54, 56. A part cylindrical surface 50 of the housing includes resilient nipples 60 that engage the rockers 54, 56 to provide a frictional resistance against movement of the rockers towards or away from an operable position in which the arcuate seal members 35, 36 are concentric with the axis of the cannula. For instance, during use, rocker 54 can be freely pivoted to the position shown in FIG. 7a in which the nipple 60 begins to engage the rocker 54. In order to rotate the rocker further towards the concentric position, the nipple must deform. The deformed nipple presses on the underside of the rocker creating friction resisting movement of the rocker. When the rocker reaches a concentric position, as shown in FIG. 7b, the nipple is aligned with a circular recess 90 in the rocker which allows the nipple to return to its original shape. In order to misalign the rocker from this position it is necessary to deform the nipple. It has been found that this arrangement provides sufficient friction resistance against the movement of the rockers away from the operable position, such that the cannula will move within the patient before the rocker moves in relation to the housing.

Figure 8:
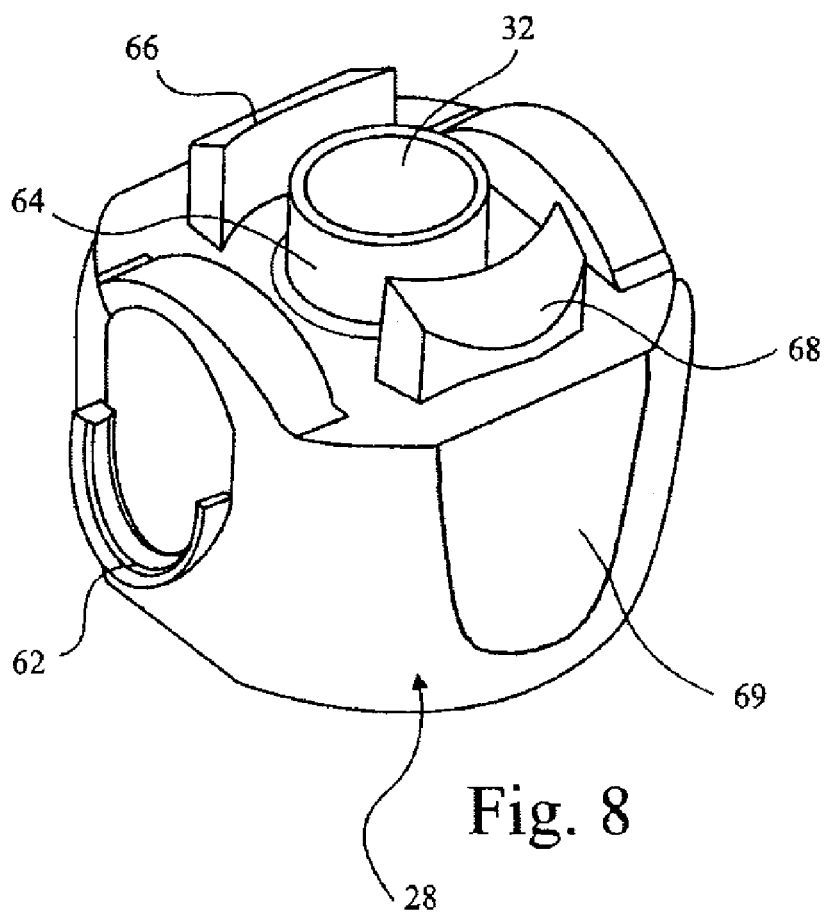
FIG. 8 is a perspective view of a housing 28.

FIG. 8 shows the cannula housing in more detail. A semi-annular protrusion 62 extends from either side of the housing. A central axially facing aperture 32 is defined in the housing 28 by a tubular section having an outside wall 64. Two clips 66, 68 are formed on the top of the housing. The clips 66, 68 create overhanging ledges 69. The semi-annular protrusion 62, tubular section, and clips 66, 68 are formed integrally to the housing 28.

Figure 9:
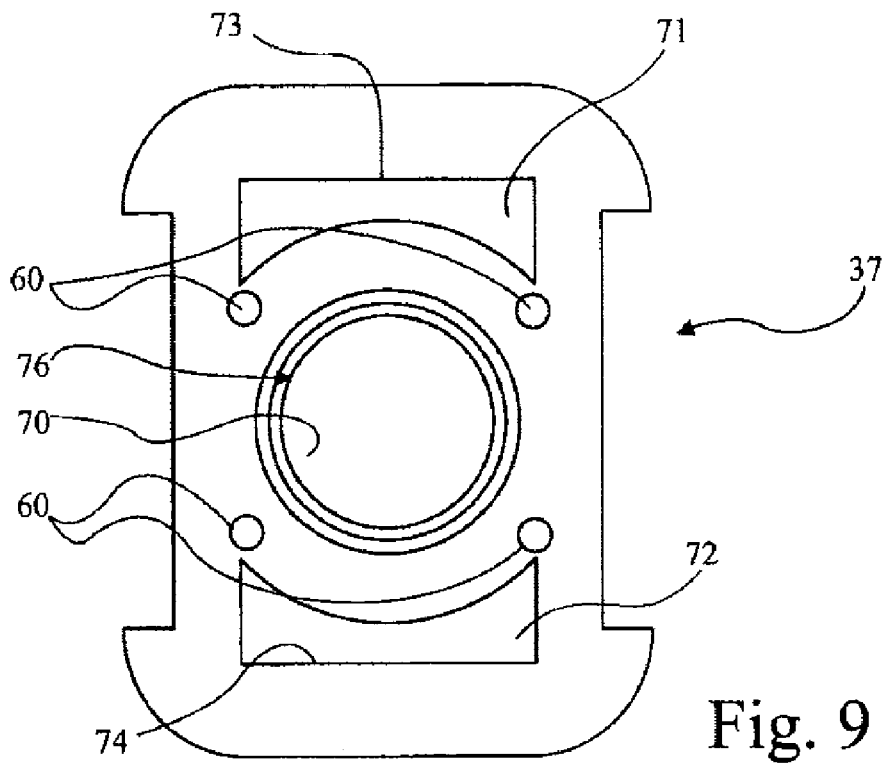
FIG. 9 is a top view of a seal for use with the housing shown in FIG. 8.

FIG. 9 shows a seal 37 that clips onto the housing 28. This seal 27 is made from a resilient material. The seal 37 includes a central hole 70 and two opening 71, 72 located on either side of the central hole 70. The opening 71, 72 corresponds to the clips 66, 68 of the housing. Accordingly, the seal 37 can be assembled on to the housing by stretching the openings over the clips 66, 68 and locating an area of the seal adjacent to the flat edge 73, 74 of the openings under the ledges 69. The seal 27 is sized so as to be stretched or alternatively or additionally slightly compressed when fitted under the ledges 69. This ensures that the seal 37 is held firmly to the housing thereby creating a seal. The central hole 70 is also sized so as to fit tightly about the outside wall 64 of the tubular section 64. The central hole 70 comprises a stepped bore wherein a thin section of the seal 37 extends over the top of the tubular section and restricts the aperture 32. When assembled to the housing 28 the edge of the central hole 70 thereby creates a lip seal against suitably sized surgical instruments that are inserted through the housing.

The seal 37 prevents fluid from escaping the housing through the central axially facing aperture 32 by forming a seal against the top of the tubular section, the outside wall 64 and the top of the housing 28. This creates a large surface area against which to seal. Furthermore the top of the tubular section acts as a support for the seal and the seal may be resiliently biased against the top of the tubular section.

When assembled to the housing the seal creates an outer profile substantially as herein described wherein the top of the housing presented to the rockers forms a part cylindrical surface. The seal also includes nipples 60. Although four nipples are shown, the function provided by the nipples can be equally achieved with one or two nipples or a plurality of nipples in various arrangements. The part cylindrical profile is also interrupted by an annular ridge 76 that is formed around the central hole 70. The ridge is raised from the top of the seal.

Figure 10:
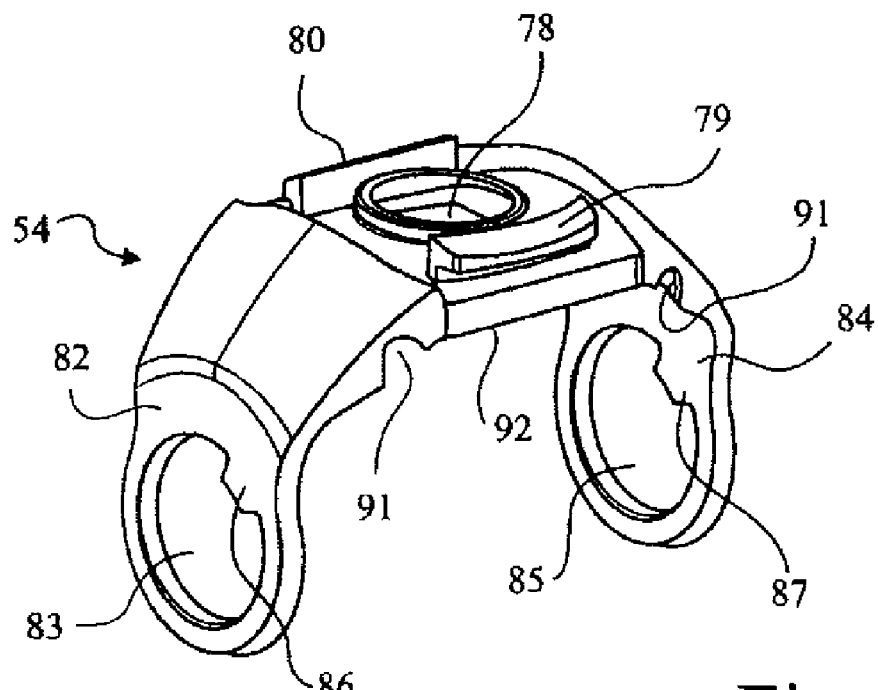
FIG. 10 is a perspective view of a pivot member for use with the housing shown in FIG. 8.

FIG. 10 shows the rocker 54. The rocker 56 is similar. The top of the rocker 54 is arranged to accept a seal 34, 36, wherein the seal 34, 36 is similar to seal 37 as described above. The rocker 54, 56 includes a central hole 78 and two clips 79, 80 on either side of the hole. Again the seal (not shown) is assembled to the rocker 54, 56 by stretching the openings over the clips 79 and locating an area of the seal under the ledges there formed. Again the seal extends over a tubular section defining a central hole with the same features as that of the seal for the housing.

Each rocker 54, 56 includes arms 82, 84. The arms include circular apertures 83, 85, which are sized to fit about the semi-annular protrusions 62 on the housing 28. Stop members 86, 87 project inwardly. When assembled to the housing 28 the stop members 86 abut the ends of the semi-annular protrusion 62 to restrict the movement of the rocker 54,56. The rockers 54, 56 are sized differently so that the arms of one rocker may fit inside the arms of the other rocker, when both are assembled to the housing.

Figure 11:
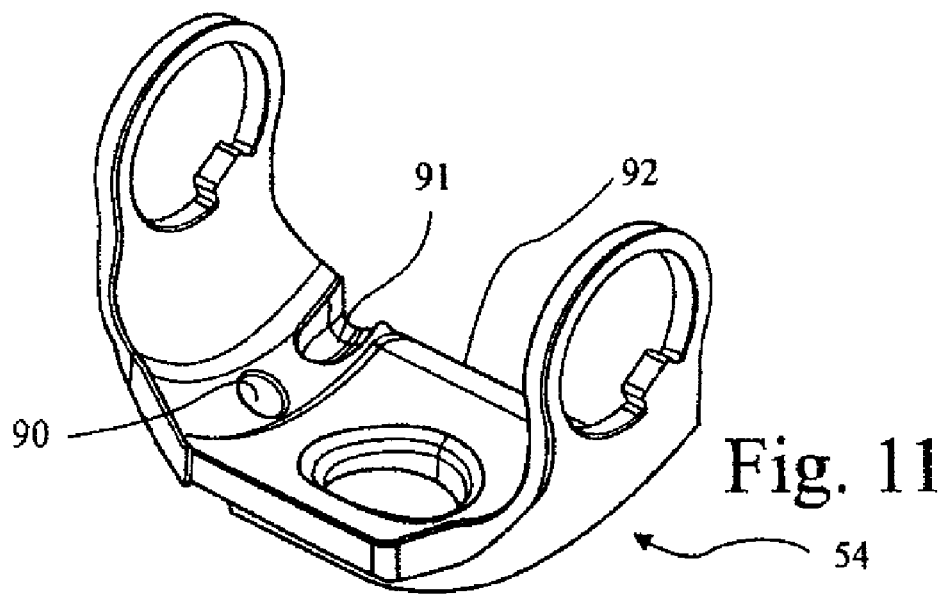
FIG. 11 is a bottom facing view of a pivot member for use with the housing shown in FIG. 8.

FIG. 11 shows the underside of the rocker 54. The rocker 58 is similar. The circular recess 90 is formed so that, when the rocker is in the concentric position, the circular recess 90 and corresponding nipple 60 is aligned. A guide channel 91 is formed extending from a leading edge 92 of the rocker. The guide channel 91 comprises a first section that is sized so as to accommodate the nipple, without deforming the nipple. A second section of the channel is ramped so as to initiate the compressing of the nipple. The end of the second section is spaced from the circular protrusion.

When the rocker 54 is assembled to the housing 28, the rocker can pivot between the inoperable and operable positions by rotating about the semi-annular recesses. As mentioned, the movement is limited by abutment of the stop member. The rockers 54 and 56 may be moved between the inoperable position and the operable, concentric position, by rotating the rockers. By way of example, rocker 54 may be rotated manually towards the concentric position. As the leading edge 92 moves over the annular ridge 76, it compresses the ridge thereby forming a seal between the ridge and underside of the rocker. When the leading edge reaches the nipple, the channel 91 first accommodates the nipple in the first section, without deforming the nipple. As the rocker is moved further, the nipple engages the ramped section of the channel 91 and the nipple is urged to compress. Maximum friction is created as the compressed nipple moves between the channel 91 and circular recess 90. When aligned with the circular recess, the nipple locates therein. This acts to provide a 'click' functionality to the rocker such that the rocker 'clicks' into the concentric position. The rocker can be moved back to the stored position in a reverse of the above process.

Each of the three seals provided by the housing or the rockers when in place, is effected by a seal whose inner opening for the instrument is very close to the inner edge of the tubular member that the seal is biased towards. This ensures good support for each seal. The radial distance from the opening of the seal to the inner edge of the supporting tubular housing may be substantially the same for all three seals.

The frictional resistance provided by each seal may be the same.

Either rocker may be moved manually or by an instrument of the surgeon that may subsequently extend through the cannula. Whilst two rockers have been described only one may be present.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A cannula sealing apparatus comprising seal members each having a different sized aperture with which, in use, surgical instruments of different sizes may be inserted in a first direction to seal with a selected seal member, at least one of the seal members being pivotable from an operative position in which a surgical instrument in use is inserted in the first direction to seal with that member and an inoperative position, the pivot axis of the pivotal movement of the seal member being in a second direction, transverse to the first direction, the apparatus further including an opening in a housing of the apparatus through which, in use, a surgical instrument is arranged to be inserted in the first direction with the seal effected by the seal members being arranged to be in the region of that opening wherein the pivotal axis of the seal member is spaced from the opening in the housing in a direction extending in the first direction.

2. A cannula sealing apparatus as claimed in claim 1 in which the pivotal axis of the seal member is arranged, in use, to pass through an inserted surgical instrument.

3. A cannula sealing apparatus as claimed in claim 1 in which the seal member includes spaced pivotal mountings on each side of the apparatus.

4. A cannula sealing apparatus as claimed in claim 1 in which the pivotally movable seal member includes a surface that is arranged, in use, to surround and seal with the surface of the housing that surrounds the opening.

5. A cannula sealing apparatus as claimed in claim 4 in which the surfaces of the seal member and housing are part cylindrical.

6. A cannula sealing apparatus as claimed in claim 4 in which the surfaces of the seal member and the housing are part spherical.

7. A cannula sealing apparatus as claimed in claim 1 including at least two pivotally movable seal members.

8. A cannula sealing apparatus as claimed in claim 7 in which, when both of the pivotally movable seal members are in the inoperative position, the seal of each seal member is located to a different side of the first direction.

9. A cannula sealing apparatus as claimed in claim 7 in which each seal member is pivotally movable about the same pivot axis.

10. A cannula sealing apparatus as claimed in claim 9 in which, in the region of the pivot axis, the at least one seal member is axially inwards of the other seal member.

11. A cannula sealing apparatus as claimed in claim 1 in which the seal members are provided on a first part of the apparatus that is detachable from a second part of the apparatus.

12. The cannula sealing apparatus as claimed in claim 1 wherein, when each pivotable seal member is in the operable position, the pivotable seal member is restricted by a friction member such that the frictional member restricts movement of the seal member away from the operable position.

13. The cannula sealing apparatus as claimed in claim 12 wherein, engagement of the friction member when the pivotable member moves between the positions, causes the friction member to deform.

14. The cannula sealing apparatus as claimed in claim 13, wherein when the pivotable member moves from the inoperative position to the operative position, during at least part of that movement, the friction member has no effect.

15. The cannula sealing apparatus as claimed in claim 1 wherein at least one seal is resilient, the resilient seal including a circular opening that is supported by an adjacent non-resilient raised circular support of greater diameter than that of the resilient seal with the resilient seal being biased towards the circular support.

16. A method of using a cannula sealing apparatus that comprises a plurality of seal members each having a different sized aperture with which, in use, a surgical instrument of a different size can be inserted in a first direction through an opening in a housing to seal with a selected seal member in the region of the opening in the housing and in which at least one seal member is pivoted about an axis of the seal member spaced from the opening in the housing in a direction extending in the first direction from an operative position in which, a surgical instrument may, in use, be inserted in the first direction to an inoperative position, the seal member being pivoted about an axis extending in a second direction, transverse to the first direction to move between the operative and inoperative positions.

17. A method of using a cannula sealing apparatus as claimed in claim 16 comprising inserting a surgical instrument of first size in a first direction to seal with a seal member of a first size aperture and then removing that instrument and subsequently pivoting at least one seal member about its axis from an inoperative position to an operative position in which a second surgical instrument of a different size to the first instrument is moved in the first direction to seal with the seal member of a different size.

18. A method of using a cannula sealing apparatus as claimed in claim 17 wherein the method comprises moving the instrument in order to pivot each sealing member between the inoperative and operative positions.

19. A method of using a cannula as claimed in claim 16 comprising inserting a surgical instrument through the cannula along the first axis, and, before inserting the surgical instrument, selecting an appropriately sized seal member so that the selected seal member seals against the instrument, the method including causing a frictional member to engage the seal member, when the seal member is in the operable position, such that the frictional member restricts the seal member from moving away from the operable position.

20. A method of using a cannula as claimed in claim 16 comprising pivoting one of at least two pivotally movable seal members about an axis common to the seal members with one seal member being axially inwards of the other seal member in the region of the pivot axis.

* * * * *